United States Patent [19]

Whalen

[11] 4,130,904
[45] Dec. 26, 1978

[54] PROSTHETIC BLOOD CONDUIT

[75] Inventor: Robert L. Whalen, Cambridge, Mass.

[73] Assignee: Thermo Electron Corporation, Waltham, Mass.

[21] Appl. No.: 803,904

[22] Filed: Jun. 6, 1977

[51] Int. Cl.$^2$ ............................................. A61F 1/24
[52] U.S. Cl. .................................. 3/1.4; 128/334 R; 138/122
[58] Field of Search .................... 3/1, 1.4; 128/334 R; 138/121, 122, 123, 124, 138, 177

[56] References Cited

U.S. PATENT DOCUMENTS

| | | | |
|---|---|---|---|
| 2,321,064 | 6/1943 | Broedling | 138/122 X |
| 2,683,466 | 7/1954 | Guiles | 138/122 X |
| 3,076,737 | 2/1963 | Roberts | 138/122 X |
| 3,152,618 | 10/1964 | Rothermel et al. | 138/122 |
| 3,272,204 | 9/1966 | Artandi et al. | 3/1 X |
| 3,304,557 | 2/1967 | Polansky | 3/1.4 |
| 3,316,557 | 5/1967 | Liebig | 3/1.4 |
| 3,479,670 | 11/1969 | Medell | 3/1.4 |
| 3,562,820 | 2/1971 | Braun | 3/1.4 |
| 3,588,920 | 6/1971 | Wesolowski | 3/1.4 |
| 3,688,317 | 9/1972 | Kurtz | 3/1.4 |

OTHER PUBLICATIONS

"USCL Sauvage External Dacron Velour Prosthesis", USCL Brochure, 6 pages, Box 566 Billerica, Mass. 01821, 3-73.
"Porosity", Primary Determinant of Ultimate Fate of Synthetic Vascular Grafts", Wesolowski, Surgery, vol. 503, #1, Jul. 61.

Primary Examiner—E. H. Eickholt
Attorney, Agent, or Firm—James L. Neal; Herbert E. Messenger

[57] ABSTRACT

A prosthetic blood conduit comprises two porous concentrically associated tubes with a helical spring enclosed therebetween. Spring strength and frictional engagement between the spring and tubes enables the conduit to resist collapse under a wide variety of stress forces. Convolutions in the tube walls provide flexibility without kinking.

7 Claims, 2 Drawing Figures

PROSTHETIC BLOOD CONDUIT

BACKGROUND OF THE INVENTION

This invention relates generally to blood conduits and in particular to implantable prosthetic blood conduits.

Prosthetic blood conduits have become valuable in modern medicine. They can be used as either permanent or temporary arterial prostheses. One of the requirements of many such conduits is that they maintain a stable biological interface between the blood stream and the conduit wall. Another requirement is resistance to collapse under a wide variety of stress forces while maintaining flexibility.

Accordingly, it it an object of the present invention to provide a prosthetic blood conduit capable of maintaining a stable biological interface between the conduit wall and the blood flow.

Another object of the present invention is to provide a flexible blood conduit which can prevent interference with the blood flow under a wide variety of stress forces.

SUMMARY OF THE INVENTION

A prosthetic blood conduit is provided by two concentrically associated polyester fabric tubes and a coil spring enclosed therebetween. The wall of each fabric tube, usually woven or knitted, is constructed in a convoluted manner to afford flexibility for bending without kinking and some radial strength. The major part of the radial strength is supplied by the enclosed spring. Additional strength to resist collapse forces results from frictional engagement between the coil spring and the fabric tubes. The structure maintains the flexibility necessary for surgical use while maintaining a near full lumen diameter under various stress forces and in various configurations for connection. The convoluted wall of each tube is porous to aid the growth of a stable biological interface.

DETAILED DESCRIPTION OF THE DRAWING

Figure 1:
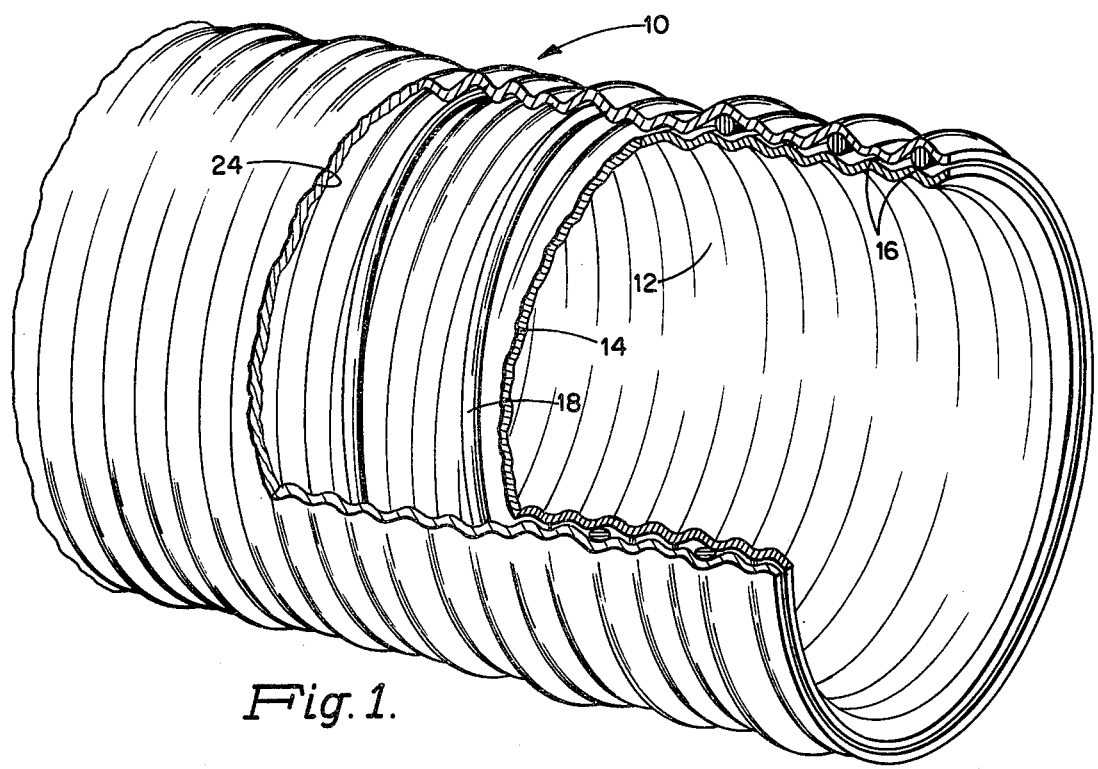
FIG. 1 shows a cut-away perspective view of a preferred embodiment of the present invention.

As shown in FIG. 1, the blood conduit 10 includes a flexible fabric tube 14 forming an inner surface 12. The wall of the inner tube 14 forms a continuous series of helical convolutions 16 that allow the inner tube 14 to bend without the kinking associated with straight-walled tubes.

The wall of the inner tube 14 is characterized by a certain porosity. Coagulation of blood on the porous wall seals the inner tube 14 and forms thereon a foundation for a stable biological interface between the inner surface 12 and the blood flow. The magnitude of tube porosity suitable for any particular application is determined by the prevailing tendency of a patient's blood to coagulate, which tendency may be affected by the presence of anti-coagulant drugs in the patient's circulatory system. In surgical applications, where a patient is taking anti-coagulant drugs, it may be desirable to use a tightly woven arterial graft with minimized porosity.

A helical reinforcing spring 18 closely surrounds the inner tube 14. Radial strength afforded by the wall structure of the inner tube 14 maintains a close fit between said tube and the spring 18. The spring 18, responsible for most of the radial strength, must be sufficiently flexible to avoid substantial resistance to bending in vivo so the conduit will not interfere with natural organs. One biologically compatible material used for the spring 18 is No. 316 stainless steel. The spring may be entirely of stainless steel or coated therewith. Obviously other biologically compatible spring materials may be used.

An outer tube 24, encloses both the inner tube 14 and the spring 18. The outer tube 24 is of a diameter larger than the inner tube 14 and sufficiently small to fit snugly around the spring 18. The outer tube 24 has a convoluted wall structure similar to that of the inner tube 14 to permit the outer tube to be bent without the kinking associated with straight-walled tubes. The outer tube 24 may exhibit a porosity like that of the inner tube 14. This permits tissue ingrowth from perivascular space to anchor the biologically stable interface on the inner tube 14. Generally, the greater the degree of porosity the greater the tissue ingrowth.

Biologically compatible Dacron convoluted wall tubes, called DeBakey straight arterial grafts, are available in various diameters from the U.S. Catheter and Instrument Corporation of Billerica, Mass. Two models of different diameter suitable for use in producing the inner and outer tubes of this conduit are Nos. 007068 and 007069. A less porous graft constructed with a tighter weave fabric, useful where anti-coagulant drugs are in use, is available from Meadox Medicals Incorporated of Oakland, N.J. The graft is called Low Porosity Dacron Cooley arterial graft and models of two suitable diameters are Nos. 184418 and 184420. If the patient's blood has a very low tendency to coagulate, the graft may be preclotted with whole blood prior to implantation.

Figure 2:
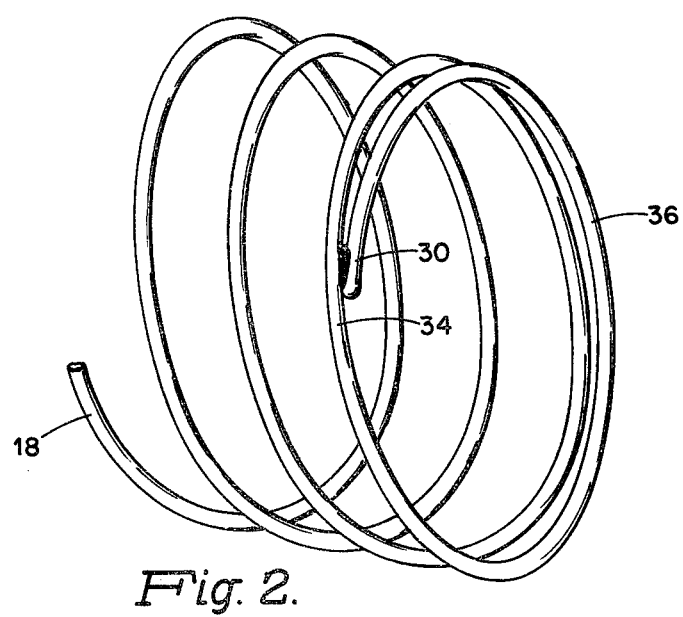
FIG. 2 is a perspective view of a coil spring which may be used in the present invention.

End terminations for the conduit may be formed in any suitable manner. General requirements are that an end termination allow a connection of the conduit which is biologically compatible and does not leak. One form of acceptable termination is shown in FIG. 2. The free end 30 of the coil spring 13 is affixed to the last preceding ring 34 to form a closed ring 36, thereby avoiding interference by the free end 30 within living tissue. One acceptable form for the affixation is welding. The dacron tubes (not shown in FIG. 2) are sutured together circumferentially to the closed ring 36 to prevent slippage along the coil and leakage upon implantation. Connection of this type of termination to an organ or artery may be accomplished by suturing the end of the conduit thereto. Where appropriate, the end of the conduit 10 may be mounted to a rigid fitting which is secured in an appropriate manner to the patient.

As described, the inner tube 14 and the outer tube 24 are are constructed with helical convolutions in the walls thereof. The reinforcing spring 18 is also described as being helical. In the construction of a conduit embodying the present invention, it is not necessary that the pitch of helical convolutions in the fabric tubes match the pitch of the spring 18. The purpose of the convolutions in the fabric tubes is to allow expansion of the wall structure when the conduit is bent, thus allowing bending without kinking. This purpose may be accomplished by convolutions which exhibit a structural pattern other than helical. As shown in FIG. 1, the pitch of the reinforcing spring 18 does not match the pitch of the convolution of the inner tube 14 or the outer tube 24. The flexibility of the conduit fabric allows crossthreading of these pitches while avoiding harmful effects to the performance.

An important feature of the combined structure is a strength factor beyond the strength of the individual components. The combined structure is capable of resisting collapse under forces comprising both axial and radial components. This strength is achieved by frictional engagement between the inner tube 14 and the spring 18, and between the spring 18 and the outer tube 24.

If a fabric graft similar to that included in the present embodiments is bent sharply, outward expansion of the conduit, in a direction perpendicular to the radius of the bend, allows collapse of the lumen diameter in both directions along the radius of the bend. In other words, those diametrically opposite portions of the conduit along the inside and outside of the bend move inward constricting the lumen while the sides between these portions expand. With the spring 18 holding the inner tube 14 in a close fit the sides of the tube 14 cannot expand outwardly and the small but significant radial strength of the tube 14 prevents collapse. Thusly, the snug fit between the inner tube 14 and the spring 18 prevents collapse of the conduit 10 when it is bent sharply.

Frictional engagement between the outer tube 24 and the spring 18 also enhances the strength of the conduit 10. Under torsional forces the outer tube 24 prevents the spring 18 from unwinding and thereby releasing its grip on the inner tube 14. Also the outer tube 24 prevents the conduit 10 from bending to too great an angle. As the conduit 10 is initially bent the wall convolutions of the outer tube 24 unfold to allow bending. Once all of the convolutions are unfolded, the outer tube 24 becomes stretched over the radially strong spring 18 thereby preventing further bending of the conduit 10. As will be understood from the above, the conduit 10 is capable of maintaining a large degree of flexibility without substantial restriction of its lumen diameter. Because of these characteristics, the conduit 10 is adaptable for a wide variety of surgical configurations. As various changes could be made in the above construction without departing from the scope of the invention, it should be understood that all matter contained in the above description or shown in the accompanying drawing shall be interpreted as illustrative and not in a limiting sense.

I claim:

1. A blood conduit, comprising:
    a flexible cylindrical inner tube having convoluted walls to provide flexibility without kinking, said inner tube being porous to promote the formation of a biologically stable interface;
    a flexible cylindrical outer tube concentrically enclosing said inner tube and having convoluted walls to provide flexibility without kinking; and
    a helical spring interposed between and frictionally engaging said outer and said inner tubes.

2. The conduit of claim 1, wherein said outer tube is porous to permit tissue ingrowth from the perivascular space.

3. The conduit of claim 1, wherein said inner tube and said outer tube comprise a woven or knitted fabric.

4. The conduit of claim 3, wherein said fabric is Dacron.

5. The conduit of claim 1, wherein said helical spring comprises a stainless steel surface.

6. The conduit of claim 1, further comprising means for affixing at least one end of said coil spring to the last respective adjacent coil of said spring to form a closed ring.

7. The conduit of claim 6, further comprising means affixing said inner and outer tubes together and circumferentially to said closed ring to form an end termination for said conduit.

* * * * *